(12) United States Patent
Weiss

(10) Patent No.: US 7,404,805 B2
(45) Date of Patent: Jul. 29, 2008

(54) ORTHOTIC DEVICE AND METHODS OF USE

(75) Inventor: Nicole M. Weiss, Ann Arbor, MI (US)

(73) Assignee: The Regents of the University of Michigan, Ann Arbor, MI (US)

(*) Notice: Subject to any disclaimer, the term of this patent is extended or adjusted under 35 U.S.C. 154(b) by 483 days.

(21) Appl. No.: 10/765,743

(22) Filed: Jan. 27, 2004

(65) Prior Publication Data

US 2005/0165337 A1  Jul. 28, 2005

(51) Int. Cl.
*A61F 13/00* (2006.01)
(52) U.S. Cl. ............................................ 602/21; 602/20
(58) Field of Classification Search ................ 602/5, 602/20, 23, 16, 21; 601/5, 33
See application file for complete search history.

(56) References Cited

U.S. PATENT DOCUMENTS

| | | | |
|---|---|---|---|
| 5,058,574 A | | 10/1991 | Anderson |
| 5,337,737 A | * | 8/1994 | Rubin et al. .................. 601/33 |
| 5,447,490 A | * | 9/1995 | Fula et al. ..................... 601/40 |
| 5,503,619 A | * | 4/1996 | Bonutti ........................ 602/16 |
| 6,866,646 B2 | * | 3/2005 | Hopkins et al. ................ 602/5 |
| 2003/0105416 A1 | * | 6/2003 | Hepburn et al. ............... 601/33 |
| 2003/0125651 A1 | * | 7/2003 | Hopkins et al. ............... 602/20 |

FOREIGN PATENT DOCUMENTS

WO   WO 92/00042   1/1992

OTHER PUBLICATIONS

Bonutti PM, Windau JE, Ables BA, Miller BG. Static Progressive Stretch to Reestablish Elbow Range Of Motion. Clinical Orthopaedics 1994;303:128-134.
Cohen E. Adjunctive Therapy Devices: Restoring ROM Outside of the Clinic. Physical Therapy Products, Mar. 1995:10-13.
Hotz M. Clinical Management of Soft Tissue Stiffness and Loss of Joint Motion. Inside Case Management 2002;8(3):11-12.
Hotz M, Bonutti P, Cremens M, Gray T, Leo C. Beyers M. Joint Contracture Rehabilitation: Static Progressive Stretch. JBJS, Orthopaedic Transactions 1998-9;22(1).
Jansen et al., Treatment of a Knee Contracture Using a Knee Orthosis Incorporating Stress Relaxation Techniques. Physical Therapy 1996,76:182-186.
Millett PJ, Johnson B, Carlson J, Krishnan S, Steadman R. Rehabilitation of the Arthrofibrotic Knee. American Journal of Orthopedics, Nov. 2003:531-538.
Schultz-Johnson K. Static Progressive Splinting. Journal of Hand Therapy, Apr.-Jun. 2002:163-178.
Bonutti, P. et al., "Joint Contracture Rehabilitation: Static Progressive Stretch" Scientific Exhibit, American Academy of Orthapaedic Surgeons Meeting—Poster Presentation, Mar. 1998.

(Continued)

*Primary Examiner*—Kim M Lewis
(74) *Attorney, Agent, or Firm*—Casimir Jones S.C.

(57) ABSTRACT

The present invention relates to orthotic devices and methods of use of orthotic devices. In particular, the present invention provides a forearm orthotic device, and related methods of use. Furthermore, the present invention provides methods for treating forearm disorders.

17 Claims, 1 Drawing Sheet

OTHER PUBLICATIONS

Donatelli, R. et al., "Using Static Progressive Stretch and Stress Relaxation in the Treatment of Glenohumeral Joint Adhesive Capsulitis," Orthopaedic Research Society Annual Meeting—Poster Presentation, Feb. 2001.

Gamage, T., et al., "The Use of Static Progressive Stretch on the Burn Joint Contracture," Podium Presentation at the American Burn Association Meeting, Mar. 24-27, 1999.

Green et al., Turnbuckle, Orthotic Correction of Elbow Flexion Contractures after acute injuries. J. Bone Joint Surg, 1970; 61A 1092-5.

Shah MA, Lopez JK, Escalante AS. Green DP. Dynamic Splinting of forearm Rotational Contracture after Distal Radius Fraction. [Journal Article] Journal of Hand Surgery—American vol. 27(3):456-63 May 2002.

Taylor et al., Viscoelastic Properties of Muscle Tendon Units—The Biomechanical Effects of Stretching, American Journal of Sprots Medicine, vol. 18#3 (1990).

Light et al., A Low Load Prolonged Stretch vs. High Load Brief Stretch in Treating Knee Contractures, Physical Therapy, 64:330 ((1984).

Nicole M. Parent, et al, Forearm Rotation Stiffness: Efficacy of Non-Operative Management with Static Progressive Splinting, Paper #30B, Oct. 5, 2002, Synergy Annual Meeting.

\* cited by examiner

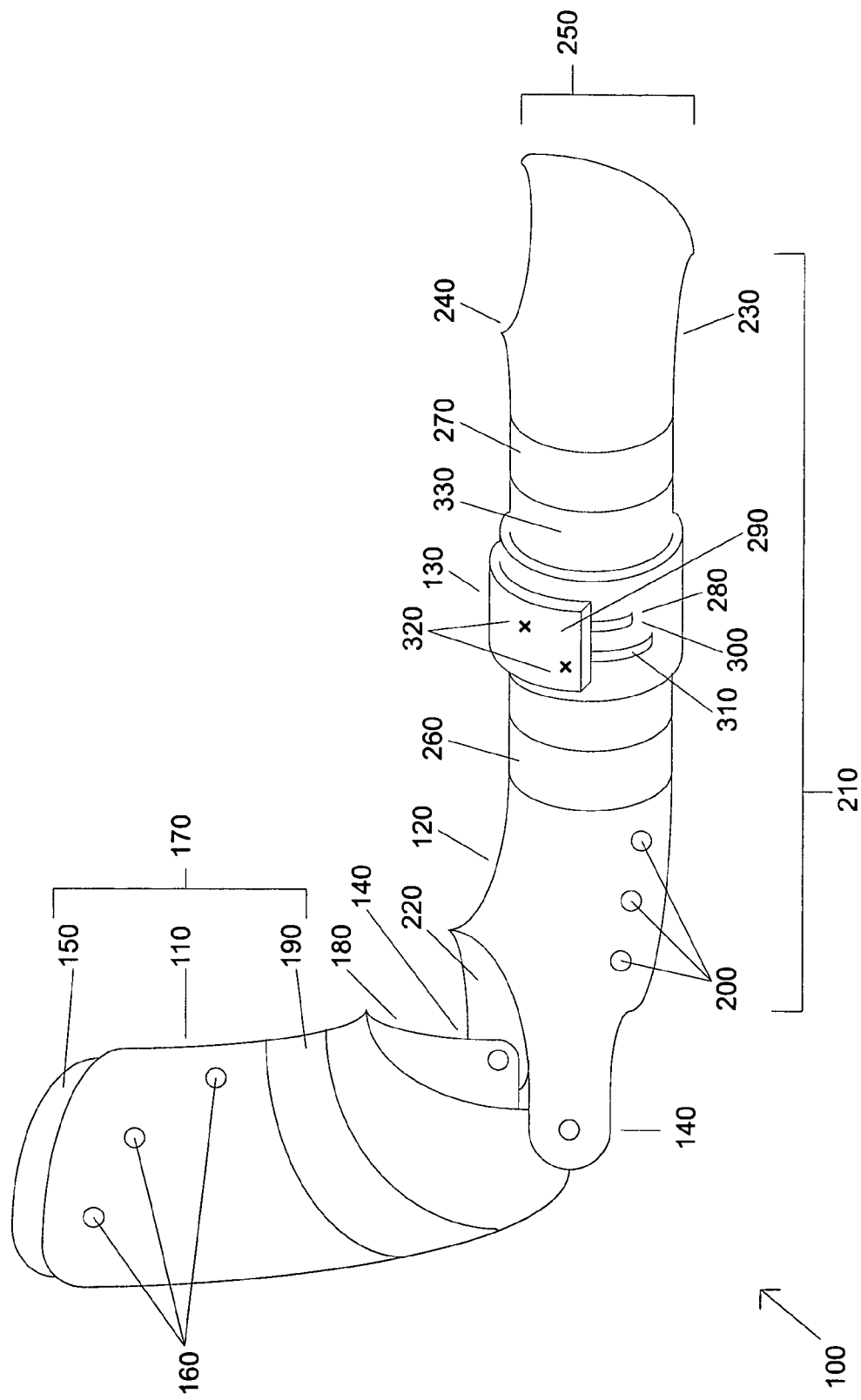

ORTHOTIC DEVICE AND METHODS OF USE

FIELD OF THE INVENTION

The present invention relates to orthotic devices and methods of use of orthotic devices. In particular, the present invention provides a forearm orthotic device, and related methods of use. Furthermore, the present invention provides methods for treating forearm disorders.

BACKGROUND

Contractures, a tendency for muscles, tendons or scar tissue to shorten in skeletal joints, are common after trauma and represent a major challenge in the care of such injuries. Routine and occupational tasks can be severely hindered by flexion-extension contractures of the humeral-ulnar joint as well as supination-pronation contractures of the proximal radial-ulnar joint which controls rotational motion of the radius about the axis of the ulna.

Current approaches to the treatment of forearm trauma have more aggressively sought to prevent contracture and stiffness through movement. Methods of rigid internal fixation with sufficient stability to allow motion within days after injury rather than closed treatment and immobilization in a cast have been developed. In the treatment of dislocations, protected early motion is now begun as soon as the patient is comfortably able to do so.

However, the currently available techniques for the prevention and treatment of contracture are not uniformly successful. Early active motion alone can reduce the severity of contracture, but requires the patient's own strength, compliance and constant effort. Dynamic splints may be used, but these require pressure on the sometimes sensitive or injured soft tissues of the arm and forearm and thus may reduce patient compliance, or may not be possible to use, i.e., in burn injury. Additionally, fractures of the proximal radius that require distraction have been treated in the past with simple pin fixation holding the ulna fixed to the radius. While fixed to the ulna, contracture and loss of motion occur.

What is needed are improved methods of preventing and/or treating tissue contractures. In addition, what is needed are improved devices useful in preventing and/or treating tissue contractures.

SUMMARY

The present invention relates to orthotic devices and methods of use of orthotic devices. In particular, the present invention provides a forearm orthotic device, and related methods of use. Furthermore, the present invention provides methods for treating forearm disorders.

In preferred embodiments, the present invention provides an orthotic forearm device comprising an upper portion configured to attach to an upper arm, a lower portion configured to attach to a forearm, and a rotation component positioned around the lower portion, wherein the rotation component is configured to exert static progressive stretch upon a forearm contained in the lower portion, wherein the static progressive stretch comprises supinated static progressive stretch and pronated static progressive stretch. In further embodiments, the orthotic device is configured to serve as a stretching splint and/or a free motion brace.

In further embodiments, the lower portion comprises a mechanical axis, wherein the forearm comprises an anatomical axis, wherein the mechanical axis matches the anatomical axis. In alternative preferred embodiments, the upper portion and said lower portion comprise a thermoplastic coating (e.g., polyethylene plastic, polypropylene plastic). In preferred embodiments, the thermoplastic coating is polyethylene plastic. In further embodiments, the polyethylene plastic is greater than 3/16 inch thick.

In other preferred embodiments, the rotation component comprises a lower band and an upper plate, wherein the lower band wraps around the lower portion, wherein the lower band comprises two offset channels, wherein the upper plate is positioned over the two offset channels, wherein the upper plate comprises two screws, wherein the two screws fasten the two offset channels.

In even further preferred embodiments, the static progressive stretch is applied through twisting of the rotational component.

The present invention further provides a method of treating an forearm disorder, comprising providing an orthotic device as described above, fitting the orthotic device upon a forearm; and exerting static progressive stretch upon the forearm. In further preferred embodiments, the orthotic device further comprises an upper portion, a connecting component, a lower portion, and a rotation component, wherein the rotation component is configured to exert the static progressive stretch upon the lower portion, wherein the connecting component connects the lower portion and the upper portion. In even further embodiments, the static progressive stretch comprises supinated static progressive stretch and pronated static progressive stretch.

FIGURE DESCRIPTION

FIG. 1 illustrates an orthotic device of the present invention.

DETAILED DESCRIPTION

The present invention provides an orthotic device and related methods of use. The illustrated and preferred embodiments discuss these techniques in the context of a forearm orthotic device, and related methods of treating forearm disorders. However, it should be appreciated that the invention is applicable for use with alternate body parts, and in treating alternative disorders.

FIG. 1 shows various preferred embodiments of the orthotic device of the present invention. The present invention is not limited to these particular embodiments.

Forearm Orthotic Device

FIG. 1 illustrates a forearm orthotic device 100 of the present invention. Generally, the forearm orthotic device 100 is used in treating arm disorders. In particular, the forearm orthotic device 100 is used in treating forearm disorders involving diminished forearm range of motion (e.g., forearm rotation range of motion). The forearm orthotic device 100 restores forearm range of motion (e.g., forearm rotation range of motion) through application of static progressive stretch. In preferred embodiments, the forearm orthotic device 100 comprises an upper portion 110, a lower portion 120, a rotational component 130, and a connection joint 140. In preferred embodiments, the forearm orthotic device 100, and its respective components, is custom molded from a cast taken of an individual in a position of neutral forearm rotation and 90 degrees of elbow flexion.

Still referring to FIG. 1, the upper portion 110 serves to secure an arm above the elbow. In preferred embodiments, the upper portion 110 is custom molded to fit an individual's arm above the elbow. The upper portion 110 is not limited to a particular type of material (e.g., metal, plastic, wood, thermoplastic) or mixture of such materials. In preferred embodiments, the upper portion 110 comprises a thermoplastic coating (e.g., polyethylene plastic, polypropylene plastic). The upper portion 110 is not limited to a particular material thickness. In preferred embodiments, the upper portion 110 is greater than 3/16 inch thick. In further preferred embodiments, the upper portion 110 is 1/8 inch thick. The upper portion 110 is not limited to a particular type of interior lining material 150 (e.g., Aliplast; Plastizote; P-Lite). In preferred embodiments, the upperportion 110 interior lining material 150 is Aliplast. The upper portion 110 interior lining material 150 is not limited to a particular thickness. In preferred embodiments, the thickness of the upper portion 110 interior lining material 150 is 3/16 inch thick. The upper portion 110 is not limited to a particular length. In preferred embodiments, the length of the upper portion 110 measures from the individual's elbow to below the individual's shoulder. In some embodiments, the upper portion 110 comprises a plurality of upper portion vents 160. In preferred embodiments, the upper portion 110 comprises at least one upper portion vent 160.

The upper portion 110 is not limited to a particular shape. In preferred embodiments, the shape of the upper portion 110 matches the anatomical shape of the individual's arm above the elbow. In preferred embodiments, the upper portion 110 further comprises an upper portion body 170 and two upper portion prongs 180. In preferred embodiments, the two upper portion prongs 180 are positioned at the lower end of the upper portion.

In some embodiments, the upper portion 110 comprises above-elbow straps 190. The above-elbow straps 190 provide support within the upper portion 110. In preferred embodiments, the upper portion 110 comprises two above-elbow straps 190. The above-elbow straps 190 are not limited to a method of attachment (e.g., glue, velcro, staples, fasteners) onto the upper portion 110. The above-elbow straps 190 are not limited to a particular location of attachment on the upper portion 110. The above-elbow straps 190 are not limited to a particular length or width. The above-elbow straps 190 are not limited to a particular method of tightening or loosening (e.g., snap, glue, hook clasp, velcro). In preferred embodiments, the above-elbow straps 190 tighten and loosen with velcro.

Still referring to FIG. 1, the lower portion 120 serves to secure an arm below the elbow. The lower portion 120 is not limited to a particular type of molding or casting (e.g., custom, mass produced). In preferred embodiments, the lower portion 120 is custom molded to fit an individual's arm below the elbow. The lower portion 120 is not limited to a particular type of material (e.g., metal, plastic, wood, thermoplastic) or mixture of such materials. In preferred embodiments, the lower portion 120 comprises a thermoplastic coating (e.g., polyethylene plastic, polypropylene plastic). The lower portion 120 is not limited to a particular material thickness. In preferred embodiments, the lower portion 120 is greater than 3/16 inch thick. In further preferred embodiments, the lower portion 120 is 1/8 inch thick. The lower portion 120 is not limited to a particular type of interior lining material 150 (e.g., Aliplast; Plastizote; P-Lite). In preferred embodiments, the lower portion 120 interior lining material 150 is Aliplast. The lower portion 120 interior lining material 150 is not limited to particular thickness. In preferred embodiments, the interior lining material 150 of the lower portion 110 is 3/16 inch thick. The lower portion 120 is not limited to a particular length. In preferred embodiments, the length of the lower portion 120 measures from the individual's elbow to beyond the individual's hand. In further embodiments, the lower portion 120 immobilizes an individual's wrist. In some embodiments, the lower portion 120 comprises a plurality of lower portion vents 200. In preferred embodiments, the lower portion 120 comprises at least one lower portion vent 200.

The lower portion 120 is not limited to a particular shape. In preferred embodiments, the shape of the interior lining of the lower portion 120 matches the anatomical shape of the individual's forearm. In preferred embodiments, the shape of the outer lining of the lower portion 120 is round. In preferred embodiments, the lower portion 120 further comprises a lower portion body 210 and two lower portion prongs 220. In preferred embodiments, the two lower portion prongs 220 are positioned at the upper end of the lower portion 120. In further preferred embodiments, the lower portion 120 extends beyond the wrist area 230. In further embodiments, the lower portion 120 comprises a thumb opening 240 and a finger(s) opening 250. In further preferred embodiments, the shape of the lower portion 120 immobilizes the wrist of an individual in a neutral position (e.g., the palm internally rotated in parallel with the sagittal plane; the wrist is immobilized in terms of flexion and extension). In other preferred embodiments, the wrist is immobilized from flexion but may be extended slightly. In even further preferred embodiments, application of the rotation component 130 results in rotation of the palm while the wrist remains immobilized.

In some embodiments, the lower portion 120 comprises below-elbow straps 260. The below-elbow straps 260 provide support within the lower portion 120. In preferred embodiments, the lower portion 120 comprises one below-elbow strap 260. The below-elbow straps 260 are not limited to a method of attachment (e.g., glue, velcro, staples, fasteners) onto the lower portion 120. The below-elbow straps 260 are not limited to a particular location of attachment on the lower portion 120. The below-elbow straps 260 are not limited to a particular length or width. The below-elbow straps 260 are not limited to a particular method of tightening or loosening (e.g., snap, glue, hook clasp, velcro). In preferred embodiments, the below-elbow straps 260 tighten and loosen with velcro.

In some embodiments, the lower portion 120 comprises distal wrapping straps 270. The distal wrapping straps 270 provide support within the lower portion 120. In preferred embodiments, the lower portion 120 comprises one distal wrapping strap 270. The distal wrapping straps 270 are not limited to a method of attachment (e.g., glue, velcro, staples, fasteners) onto the lower portion 120. The distal wrapping straps 270 are not limited to a particular location of attachment on the lower portion 120.

The distal wrapping straps 270 are not limited to a particular length or width. The distal wrapping straps 270 are not limited to a particular method of tightening or loosening (e.g., snap, glue, hook clasp, velcro). In preferred embodiments, the distal wrapping straps 270 tighten and loosen with velcro.

Still referring to FIG. 1, the connection joints 140 serve to provide a free motion overlapping joint between the upper portion 110 and the lower portion 120. In some embodiments, the connection joints 140 provide a free motion joint with no restrictions or stops within the joint. In further embodiments, the connection joints 140 permit free motion in the sagittal plane and preclude coronal motion. In further embodiments, a locking device is attached to the connection joints 140 allowing the elbow to be locked at a desired degree of elbow flexion (e.g., 90 degrees). The present invention is not limited to a particular type of locking device (e.g., Squeezing Joint With Wormgear, Euro International, Inc.; 2040-B, Becker Orthopedic). In preferred embodiments, the locking device is Squeezing Joint With Wormgear. The present invention is not limited to a particular type of connection joint. In preferred embodiments, the connection joints 140 comprise an attachment of the lower portion prongs 220 and the upper portion prongs 180. The connection joints 140 are not limited to a particular type of attachment (e.g., snaps, staple, screw, bolt) between the lower portion prongs 220 and the upper portion prongs 180. In preferred embodiments, the lower portion prongs 220 and the upper portion prongs 180 are attached with a screw (e.g., Chicago screw).

In further embodiments of the present invention, the lower portion 120 comprises a mechanical axis that matches the anatomical axis of a corresponding bone (e.g., the ulna twisting over the radius during forearm rotation). Generally, the anatomical axis of a bone is related to its structure, so that in a long bone the anatomical axis is the longitudinal axis of the shaft. The mechanical axis is related to the joint; the mechanical axis passes through the centre of the contact area between the articulating surfaces and lies at right angles to the surfaces in contact. In preferred embodiments, the mechanical axis of the lower portion 120 matches the anatomical axis of the forearm bones (e.g., the ulna twisting over the radius during forearm rotation).

Still referring to FIG. 1, the rotational component 130 serves in applying static progressive stretch to a forearm positioned within the forearm orthotic device 100. The rotational component 130 is not limited to a particular position within the forearm orthotic device 100. In preferred embodiments, the rotational component 130 is positioned at the mid-point in-between the connection joint 140 and the wrist area 230. In preferred embodiments, the rotational component 130 comprises a rotational component band 280 and a rotational component plate 290.

In preferred embodiments, the rotational component band 280 wraps around the lower portion 120. The rotational component band 280 is not limited to a particular type of material (e.g., metal, plastic, wood, thermoplastic) or mixture of such materials. In preferred embodiments, the rotational component band 280 comprises a thermoplastic coating (e.g., polyethylene plastic, polypropylene plastic). The rotational component band 280 is not limited to a particular material thickness. In preferred embodiments, the rotational component band 280 is greater than 3/16 inch thick. The rotational component band 280 is not limited to a particular length. In preferred embodiments, the length of the rotational component band 280 measures at least two inches.

In preferred embodiments, the lower portion 120 and the rotational component 130 are consistently shaped. In further embodiments, the lower portion 120 and the rotational component 130 are circularly shaped. The shaping between the lower portion 120 and the rotational component 130 permit the forearm orthotic device to be used in a plurality of manners. In preferred embodiments, the forearm orthotic device 100 of the present invention is used as a stretching splint. In other preferred embodiments, the forearm orthotic device 100 of the present invention is used as a free motion brace.

In preferred embodiments, the rotational component band 280 further comprises rotation component channels 300 running in parallel with the length of the rotational component band 280 (e.g., around the forearm). The rotation component band 280 is not limited to a particular number of rotation component channels 300. In preferred embodiments, the rotation component band 280 comprises two rotational component channels 300. The present invention is not limited to a particular length for the rotational component channels 300. In some embodiments, the length of the rotational component channels 300 is the entire distance around the rotational component band 280. In preferred embodiments, the length of the rotational component channels 300 extends around 60% of the rotational component band 280. In further preferred embodiments, the length of the rotational component channels 300 correspond with the full range of motion for both supinated forearm motion and pronated forearm motion. The depth of the rotational component channels 300 pass through the bottom of the rotational component band 280. The rotational component channels 300 are not limited to a particular width. In preferred embodiments, the width of the rotational component channels 300 is 3/4 inch. In other preferred embodiments, the width of the rotational component channels 300 is 1/8 inch. The present invention is not limited in the positioning of the rotational component channels 300 within the rotational component band 280. In even further preferred embodiments, one rotational component channel 300 matches supinated range of motion, while an additional rotational component channel 300 matches pronated range of motion. In other preferred embodiments, the positioning of the rotational component channels 300 upon the rotational component band 300 is offset (e.g., the start point of one channel is staggered from the start point of an additional channel). Offsetting the starting points of the rotation component channels 300 on the rotational component band 280 facilitates simultaneous supinated and pronated forearm motion.

In preferred embodiments, the lower portion 120 further comprises lower portion fastener sites 310 (e.g., locations where fasteners may attach). The present invention is not limited to a particular type of lower portion fastener site 310 (e.g., screw well). In preferred embodiments, the lower portion fastener sites 310 are thumbscrew wells. The present invention is not limited to a particular positioning of the lower portion fastener sites 310. In preferred embodiments, the lower portion fastener sites 310 are positioned directly beneath the rotation component channels 300. The present invention is not limited to a particular number of lower portion fastener sites 310. In preferred embodiments, a plurality of lower portion fastener sites 310 are positioned along the length of the corresponding rotational component channels 300. In further preferred embodiments, the plurality of lower portion fastener sites 310 are positioned at half inch intervals along the length of the corresponding rotational component channels 300.

In preferred embodiments, the rotational component plate 290 serves to secure the rotational component band 280 with the lower portion 120. The rotational component plate 290 is not limited to a particular type of material (e.g., metal, plastic, wood, thermoplastic) or mixture of such materials. In preferred embodiments, the rotational component plate 290 comprises a thermoplastic coating (e.g., polyethylene plastic, polypropylene plastic). The rotational component plate 290 is not limited to a particular material thickness. In preferred embodiments, the rotational component plate 290 is greater than 3/16 inch thick. The rotational component plate 290 is not limited to a particular length. In preferred embodiments, the length of the rotational component plate 290 measures at least two inches. The rotational component plate 290 is not limited to a particular width. In preferred embodiments, the width of the rotational component plate 290 is consistent with the width of the rotational component band 280.

In further preferred embodiments, the rotational component plate 290 comprises fasteners 320. In preferred embodiments, the fasteners 320 pass through the top face and bottom face of the rotational component plate 290. In further preferred embodiments, a majority of the fastener 320 is exposed after passing through the top face and bottom face of the rotational component plate 290. The present invention is not limited to a particular type of fastener 320 (e.g., screws, thumbscrews, nails, bolts, threaded fasteners). In preferred embodiments, the fastener 320 is a thumbscrew. The present invention is not limited to a particular number of fasteners 320. In preferred embodiments, two fasteners 320 are used in the present invention. The present invention is not limited in the positioning of the fasteners 320 on the rotational component plate 290.

The rotational component plate 290 is not limited to a particular method of securing the rotational component band 280 with the lower portion 120. In preferred embodiments, the rotational component plate 290 is positioned above the top face of the rotational component band 330 so that the fasteners 220 are in direct alignment with the rotational component channels 300 and the lower portion fastener sites 310. In such embodiments, the fasteners 320 are inserted into the lower portion fastener sites 310.

Application of Static Progressive Stretch

Static progressive stretch (SPS) is a technique using the biomechanical principle of stress relaxation to restore range of motion in tissue contractures. Static progressive stretching applies a force that slightly increases the elastic limit of the tissue in order to maintain the tissue at a given length. The result is relaxation of the contracted tissue and long-term elongation of the tissue. This tissue elongation occurs via reorganization of the collagen matrix without concurrent inflammation. The forearm orthotic device of the present invention is configured to apply supinated static progressive stretch and pronated static progressive stretch. In further embodiments the forearm orthotic device is configured to simultaneously apply supinated and pronated static progressive stretch. Simultaneous application of supinated and pronated static progressive stretch permits treatment of tissue contractions in alternating directions with only one orthotic device. In addition, simultaneous application of supinated and pronated static progressive stretch prevents tissue contracture resulting application of only supinated or pronated static progressive stretch. In preferred embodiments, the forearm orthotic device of the present invention is used in conjunction with a therapy protocol directed toward treating a forearm disorder (e.g., forearm tissue contracture).

The present invention is not limited in how static progressive stretch is applied. In preferred embodiments, static progressive stretch is applied through the rotational component. In such embodiments, the adjustment of the rotational component band applies a supinated or pronated static progressive stretch upon the forearm muscles. For example, pronated static progressive stretch is generated when the rotational component band is shifted in a pronated direction and the fasteners are tightened. A supinated static progressive stretch is generated when the rotational component band is shifted in a supinated direction and the fasteners are tightened.

In further embodiments, the orthotic device of the present invention is used in treating forearm tissue contractures and/or preventing tissue contracture resulting from forearm disorders (e.g., contusions, abrasions, lacerations, bone bruises, sprains, edema, ulnar neurapraxia, myositis ossificans, edema, sterile tenosynovitis, stenosing tenosynovitis, Raynaud's phenomenon, unilateral wasting, forearm fracture, wrist fracture, elbow fracture dislocation, humorous fracture, and Sudeck's Atrophy). Treatment methods involving the use of the orthotic device are not limited to a particular protocol. In some embodiments, general physical therapy guidelines are followed with treatment protocols involving the orthotic device of the present invention. In preferred embodiments, treatment methods involving the use of the orthotic device of the present invention entail fitting the orthotic device with a subject. In further preferred embodiments, treatment methods involve exerting static progressive stretch (e.g., supinated, pronated, or both) upon the forearm of a subject.

All publications and patents mentioned in the above specification are herein incorporated by reference. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

The invention claimed is:

1. An orthotic forearm device comprising an upper portion configured to attach to an upper arm, a lower portion configured to attach to a forearm while immobilizing the wrist, and a rotation component positioned around said lower portion, wherein said rotation component is configured to exert static progressive stretch upon a forearm contained in said lower portion, wherein said static progressive stretch comprises supinated static progressive stretch and pronated static progressive stretch.

2. The orthotic forearm device of claim 1, wherein said orthotic device is configured to serve as a stretching splint.

3. The orthotic forearm device of claim 1, wherein said orthotic device is configured to serve as a free motion brace.

4. The orthotic forearm device of claim 1, wherein said lower portion comprises a mechanical axis, wherein said forearm comprises an anatomical axis, wherein said mechanical axis matches the anatomical axis of said forearm.

5. The orthotic forearm device of claim 1, wherein said upper portion and said lower portion comprise a thermoplastic coating.

6. The orthotic forearm device of claim 5, wherein said thermoplastic coating comprises polyethylene plastic.

7. The orthotic forearm device of claim 6, wherein said polyethylene plastic is greater than 3/16 inch thick.

8. A method of treating a forearm disorder, comprising:
a) providing an orthotic device of claim 1;
b) fitting said orthotic device upon a forearm; and
c) exerting static progressive stretch upon said forearm.

9. The method of claim 8, wherein said orthotic device further comprises a connecting component, wherein said connecting component connects said lower portion and said upper portion.

10. The method of claim 8, wherein said static progressive stretch comprises supinated static progressive stretch and pronated static progressive stretch.

11. An orthotic forearm device comprising
an upper portion configured to attach to an upper arm, a lower portion configured to attach to a forearm, and a rotation component positioned around said lower portion,
wherein said rotation component is configured to exert static progressive stretch upon a forearm contained in said lower portion, wherein said static progressive stretch comprises supinated static progressive stretch and pronated static progressive stretch,
wherein said rotation component comprises a band and a plate, wherein said band wraps around said lower portion, wherein said band comprises two offset channels, wherein said plate is positioned over said two offset channels, wherein said plate comprises two fasteners, wherein said two fasteners secure said two offset channels, wherein said static progressive stretch is applied through twisting of said rotational component.

12. The orthotic forearm device of claim 11, wherein said orthotic device is configured to serve as a stretching splint.

13. The orthotic forearm device of claim 11, wherein said orthotic device is configured to serve as a free motion brace.

14. The orthotic forearm device of claim 8, wherein said lower portion comprises a mechanical axis, wherein said forearm comprises an anatomical axis, wherein said mechanical axis matches the anatomical axis of said forearm.

15. The orthotic forearm device of claim 8, wherein said upper portion and said lower portion comprise a thermoplastic coating.

16. The orthotic forearm device of claim 15, wherein said thermoplastic coating comprises polyethylene plastic.

17. The orthotic forearm device of claim 16, wherein said polyethylene plastic is greater than 3/16 inch thick.

* * * * *